(12) United States Patent
Yong et al.

(10) Patent No.: US 10,578,856 B2
(45) Date of Patent: Mar. 3, 2020

(54) CAMERA SKID

(71) Applicants: Metrotech Corporation, Santa Clara, CA (US); Wei Yong, Santa Clara, CA (US)

(72) Inventors: Wei Yong, Santa Clara, CA (US); Richard Jordan, Santa Clara, CA (US)

(73) Assignee: Metrotech Corporation, Santa Clara, CA (US)

( * ) Notice: Subject to any disclaimer, the term of this patent is extended or adjusted under 35 U.S.C. 154(b) by 0 days.

(21) Appl. No.: 15/533,338

(22) PCT Filed: Nov. 10, 2015

(86) PCT No.: PCT/CN2015/094196
§ 371 (c)(1),
(2) Date: Jun. 5, 2017

(87) PCT Pub. No.: WO2017/079896
PCT Pub. Date: May 18, 2017

(65) Prior Publication Data
US 2017/0371145 A1    Dec. 28, 2017

(51) Int. Cl.
*G02B 23/24*     (2006.01)
*G01N 21/954*    (2006.01)
*H04N 5/225*     (2006.01)

(52) U.S. Cl.
CPC ....... *G02B 23/2484* (2013.01); *G01N 21/954* (2013.01); *G02B 23/2476* (2013.01); *G02B 23/2492* (2013.01); *H04N 5/2252* (2013.01)

(58) Field of Classification Search
CPC ............ G02B 23/2484; G02B 23/2476; G02B 23/2492; G01N 21/954; H04N 5/2252
See application file for complete search history.

(56) References Cited

U.S. PATENT DOCUMENTS

| | | | |
|---|---|---|---|
| 4,405,973 A | * | 9/1983 | Moscarillo ................ F21K 2/06 362/190 |
| 5,571,977 A | | 11/1996 | Kip et al. |
| 6,831,679 B1 | * | 12/2004 | Olsson .................. G01N 21/954 348/241 |
| 8,289,385 B2 | | 10/2012 | Olsson et al. |
| 8,540,429 B1 | | 9/2013 | Olsson et al. |
| 2004/0083829 A1 | | 5/2004 | Chapman et al. |

(Continued)

FOREIGN PATENT DOCUMENTS

| CN | 101988902 A | 9/2014 |
|---|---|---|
| CN | 203658597 U | 9/2014 |

(Continued)

OTHER PUBLICATIONS

International Search Report for PCT Application No. PCT/CN2015/094196 issued by the State Intellectual Property Office of the P.R. China ISA dated Jul. 25, 2016; pp. 1-5.

(Continued)

*Primary Examiner* — Antoinette T Spinks
(74) *Attorney, Agent, or Firm* — Haynes and Boone, LLP (57) ABSTRACT

In some embodiments, a camera skid is presented. The camera skid includes a body into which a camera can be inserted; and a front portion received into the body, the front portion including a lip that contacts a face of the camera.

15 Claims, 7 Drawing Sheets

(56) References Cited

U.S. PATENT DOCUMENTS

| | | | | |
|---|---|---|---|---|
| 2010/0208055 A1* | 8/2010 | Olsson | .................. | H01B 7/182 |
| | | | | 348/84 |
| 2014/0285656 A1 | 9/2014 | Zink et al. | | |
| 2015/0230699 A1* | 8/2015 | Berul | ...................... | A61B 1/05 |
| | | | | 600/476 |

FOREIGN PATENT DOCUMENTS

| | | |
|---|---|---|
| JP | 4802233 B2 | 9/2014 |
| JP | 2010102244 A1 | 9/2014 |
| JP | 2013088512 A1 | 9/2014 |
| WO | WO2006127095 A1 | 9/2014 |

OTHER PUBLICATIONS

Written Opinion of the International Searching Authority for PCT Application No. PCT/CN2015/094196 issued by the State Intellectual Property Office of the P.R. China dated Jul. 25, 2016; pp. 1-4.
European Supplementary Search Report for European Application No. 15908026.6, dated Aug. 13, 2019, pp. 1-6.

* cited by examiner

CAMERA SKID

BACKGROUND

The present disclosure relates to a camera skid.

DISCUSSION OF RELATED ART

Underground pipes are often inspected with the use of cameras. The cameras are typically inserted into the pipe and are propelled down the pipe using the cabling to the camera. As such, the camera is propelled into a rough environment and often uses skid devices for protection and alignment. The camera skid holds the camera and provides alignment and protection for the camera as it is inserted into the pipe for inspection.

Therefore, there is a need for better camera skids for use with inspection cameras.

SUMMARY

In accordance with some embodiments, a camera skid is presented. The camera skid includes a body into which a camera can be inserted; and a front portion received into the body, the front portion including a lip that contacts a face of the camera.

These and other embodiments will be described in further detail below with respect to the following figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The drawings may be better understood by reading the following detailed description.

DETAILED DESCRIPTION

In the following description, specific details are set forth describing some embodiments of the present invention. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

This description and the accompanying drawings that illustrate inventive aspects and embodiments should not be taken as limiting—the claims define the protected invention. Various changes may be made without departing from the spirit and scope of this description and the claims. In some instances, well-known structures and techniques have not been shown or described in detail in order not to obscure the invention.

Additionally, the drawings are not to scale. Relative sizes of components are for illustrative purposes only and do not reflect the actual sizes that may occur in any actual embodiment of the invention. Like numbers in two or more figures represent the same or similar elements. Elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

Figure 1:
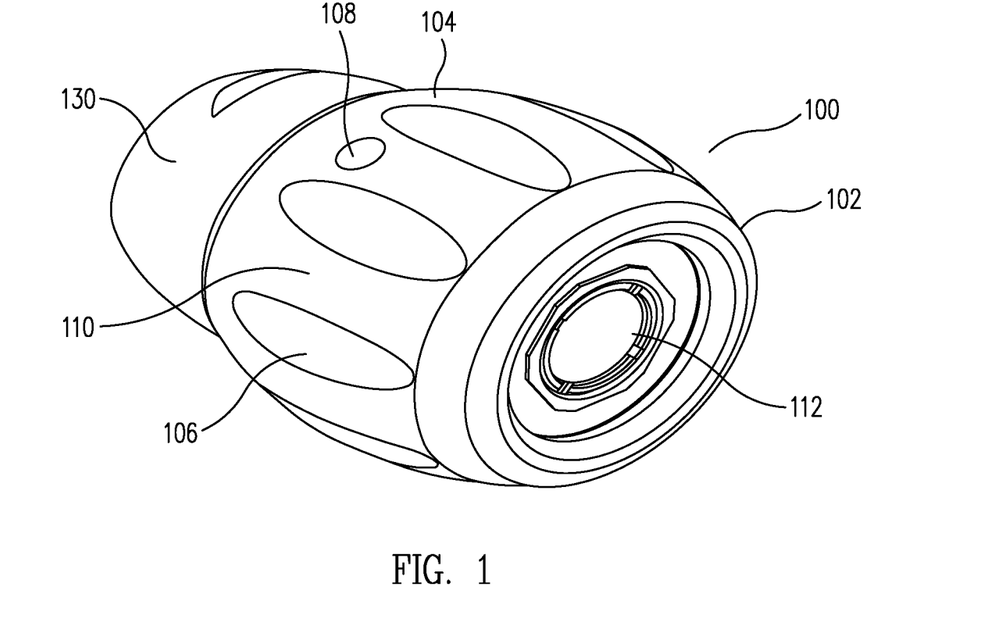
FIG. 1 illustrates a camera skid with a camera according to some embodiments of the present invention.

FIG. 1 illustrates a camera skid 100 according to some embodiments of the present invention. Camera skid 100 includes body 104 and a front portion 102. A camera 112 can be positioned through body 104 and rests on front portion 102 such that front portion 102 extends beyond the front face of camera 112. FIG. 1 illustrates a cable boot 130 contacting with body 104 of camera skid 100. Skid body 104 also includes set holes 108 that allows set screws (now shown) to contact camera 112 and rigidly hold camera 112 in place. Skid body 104 also includes ridges 110 and grooves 106 between the ridges. Ridges 110 help guide skid 100 through the pipe while grooves 106 help direct fluid in the pipe around skid 100.

As shown in FIG. 1, camera skid 100 provides protection for the face of camera 112 from offsets or debris in a pipe through which camera skid 100 is directed. Further, camera skid 100 can help center camera 112 in the pipe while keeping camera 112 off the pipe itself. By keeping camera 112 off the floor of the pipe, the spread of light provided by camera 112 can be improved, resulting in better imaging of the interior of the pipe.

Figure 2:
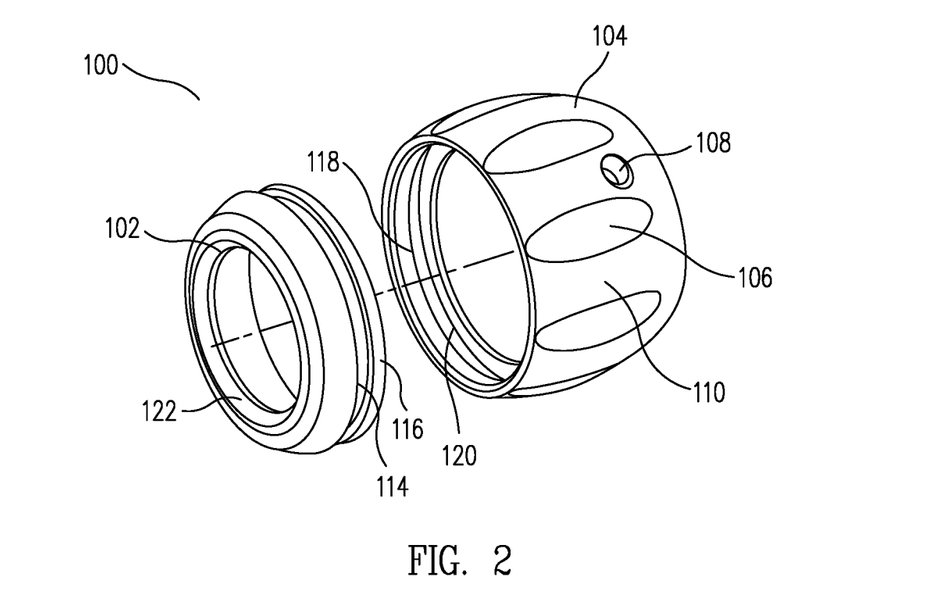
FIG. 2 illustrates a camera skid according to some embodiments of the present invention.

FIG. 2 illustrates the separated portions of skid 100, the front portion 102 and the body 104 are separated. As illustrated in FIG. 2, front portion 102 includes a lip 122 that overhangs the face of camera 112. Front portion 102 also includes a lip 116 and groove 114 that mates with a corresponding groove 118 and lip 120 on the interior of skid body 104 that receives front portion 102. Body 104 and front portion 102 are sized to receive camera 112 such that the front face of camera 112 is positioned in front portion 120 and in contact with lip 122.

Figure 3:
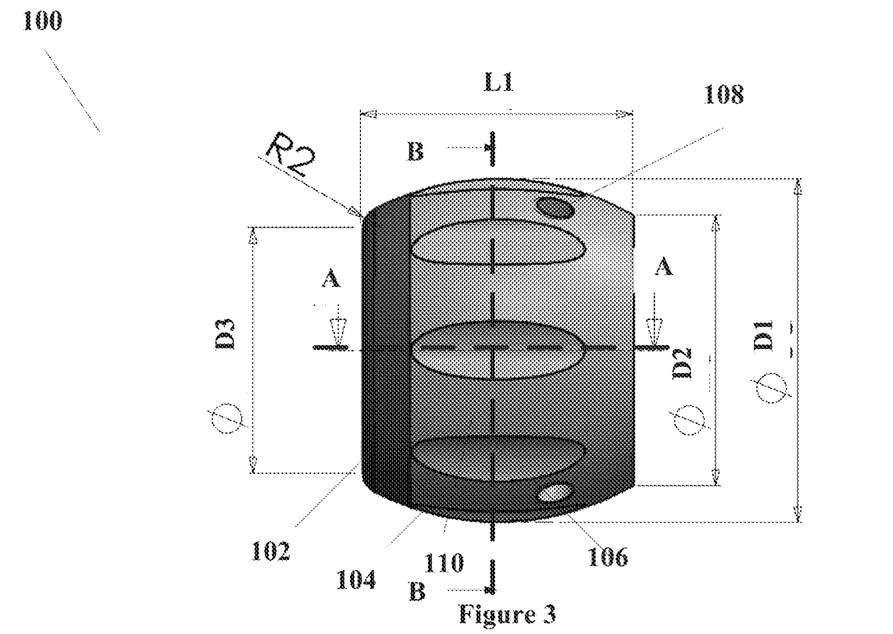
FIG. 3 illustrates dimensions of a camera skid according to some embodiments of the present invention.

FIG. 3 illustrates a side view of skid 100. As shown in FIG. 3, skid 100 has a length L1. Body 104 has a rear outer diameter D2, the rear of skid 100 being opposite front portion 102, and an outer diameter D1 across ribs 110 at their maximum diameter. The outer diameter of front portion 102 is D3.

Figure 4:
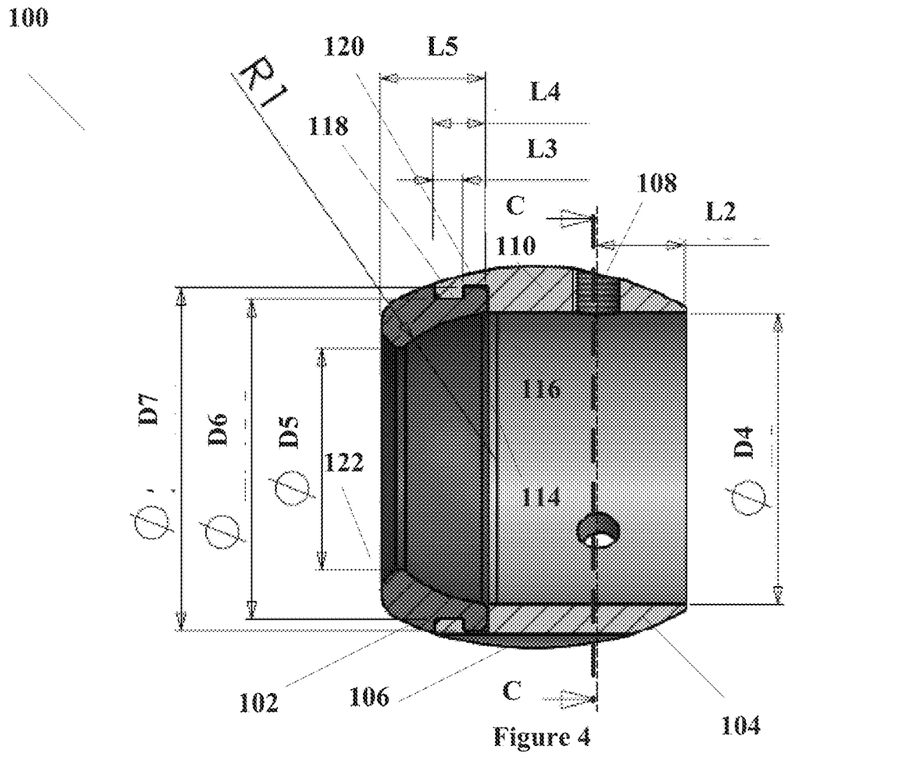
FIG. 4 illustrates dimensions of a camera skid according to some embodiments of the present invention.

FIG. 4 illustrates a cross-sectional view of skid 100 onto the plane defined by A-A illustrated in FIG. 3. As illustrated in FIG. 4, set screw hole 108 is formed in a ridge 110. Set screw hole 108 is located a distance L2 from the rear of skid 100. The inner diameter of the rear of skid 100 is D4. The innermost diameter of front portion 102 is given by D5. The outer diameter of groove 114 of front portion 102 is given by D6, which is also the inner diameter of body 104 at lip 118. The diameter of lip 116 of front portion 102 is given by diameter D7, which is also the inner diameter of groove 120 of body 104.

Figure 5:
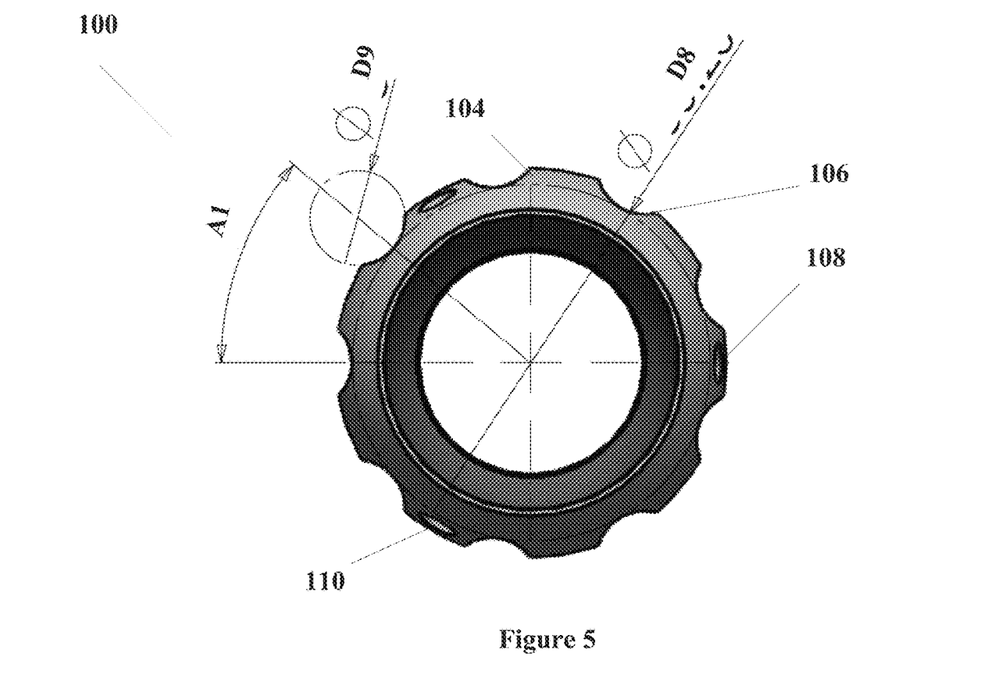
FIG. 5 illustrates another view of a camera skid according to some embodiments of the present invention.

FIG. 5 illustrates a cross-sectional view of body 104 of skid 100 through the plane indicated by B-B in FIG. 3. As shown in FIG. 5, the cross-sectional diameter between a groove 106 and a ridge 110 is given by D8. Further, grooves 106 can be defined by a circle with diameter D9. Additionally, the centers of grooves 106 are separated by an angle A1 from the center of body 104.

Figure 6:
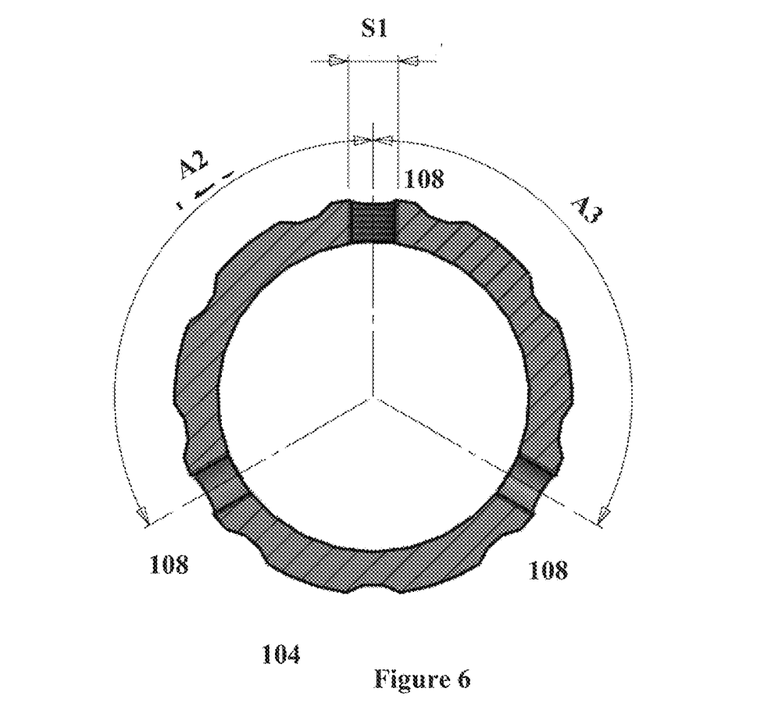
FIG. 6 illustrates another cross section of a camera skid according to some embodiments of the present invention.
Figure 7A:
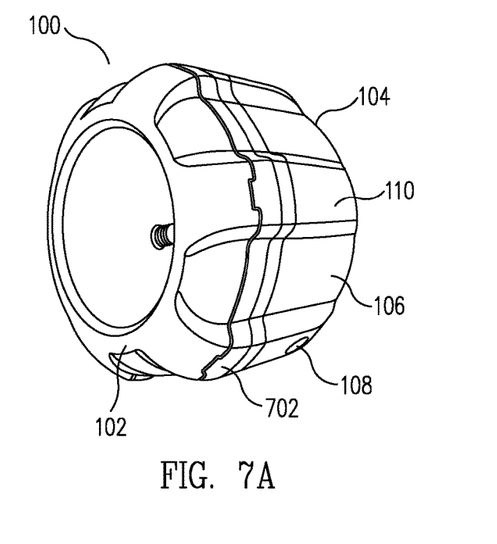
FIGS. 7A through 7E illustrates various perspectives of a camera skid according to some embodiments of the present invention.
Figure 7B:
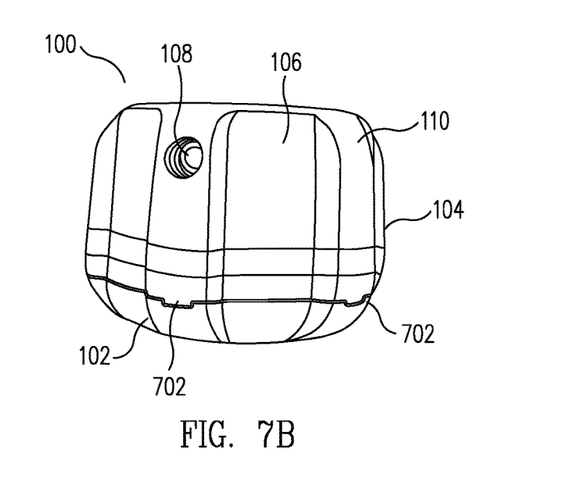
Figure 7C:
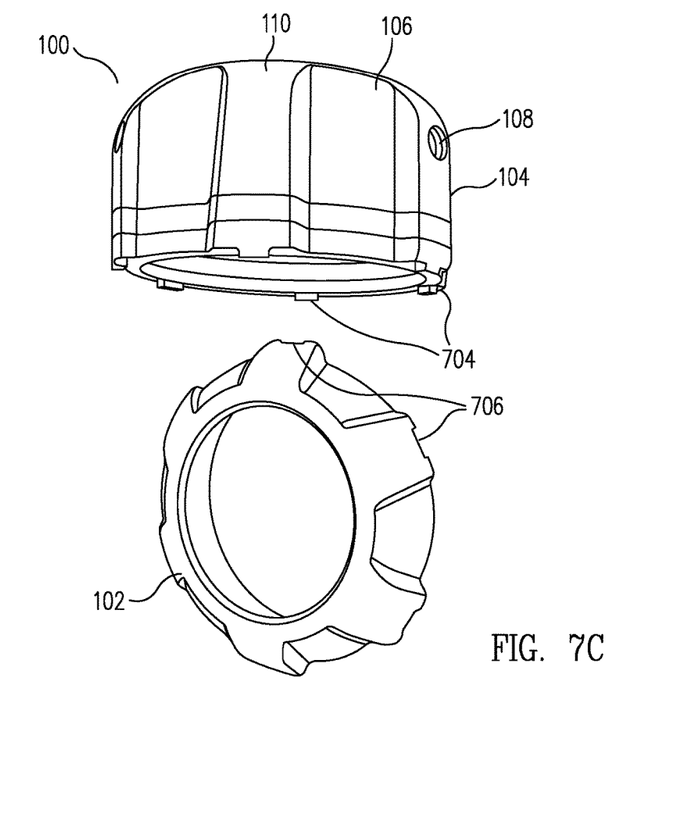
Figure 7D:
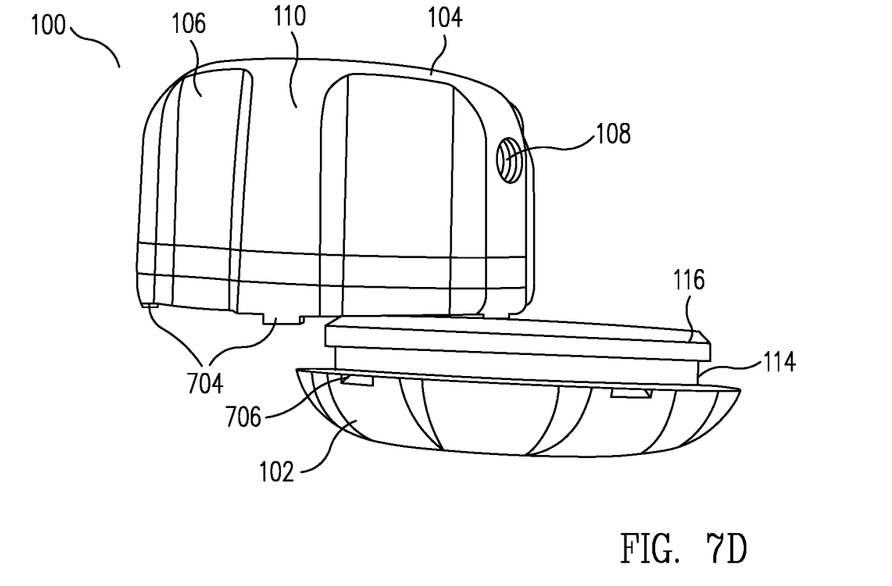
Figure 7E:
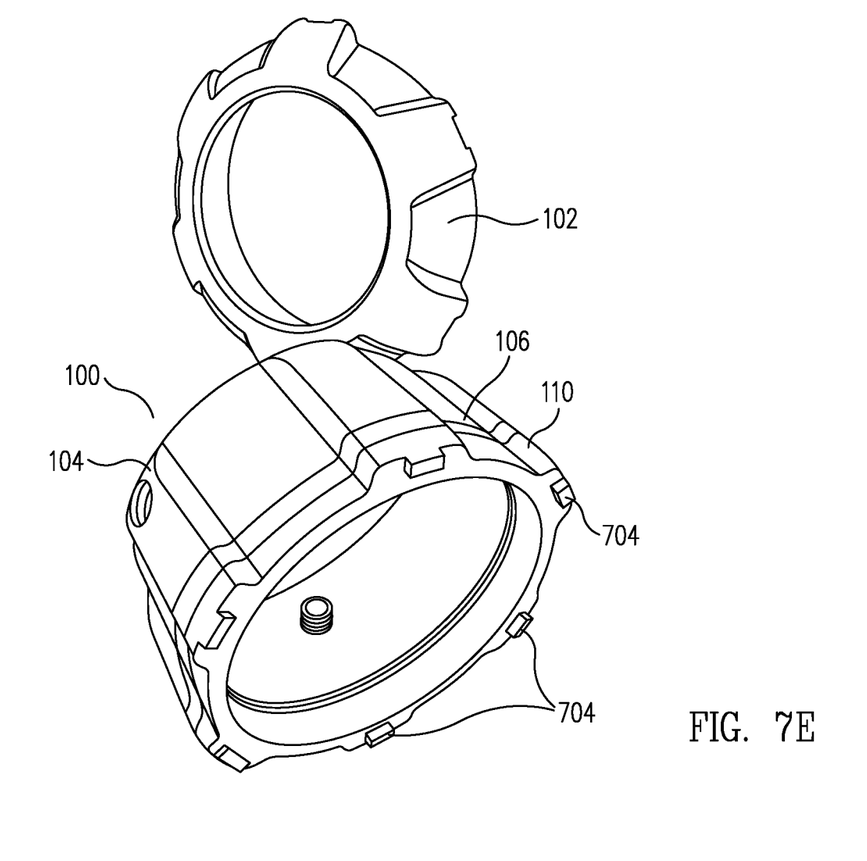
Figure 8A:
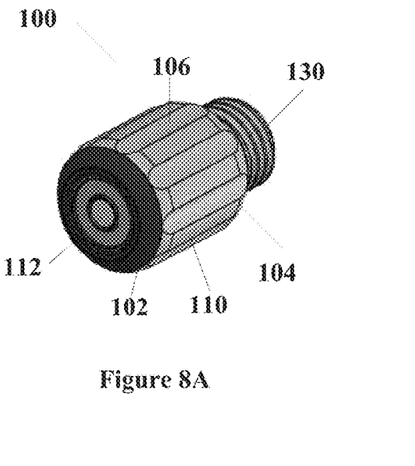
FIGS. 8A through 8E illustrates various perspectives of a camera skid according to some embodiments of the present invention.
Figure 8B:
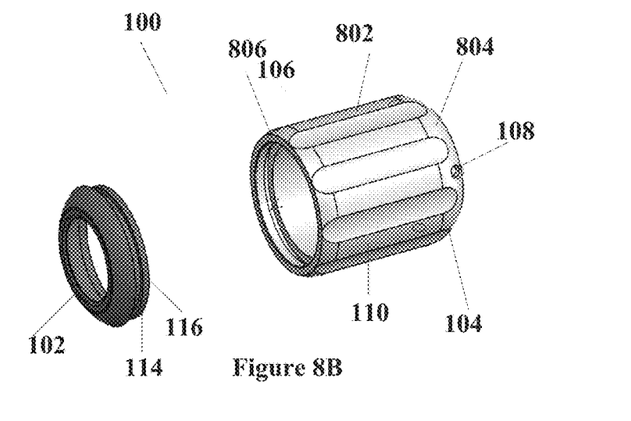
Figure 8C:
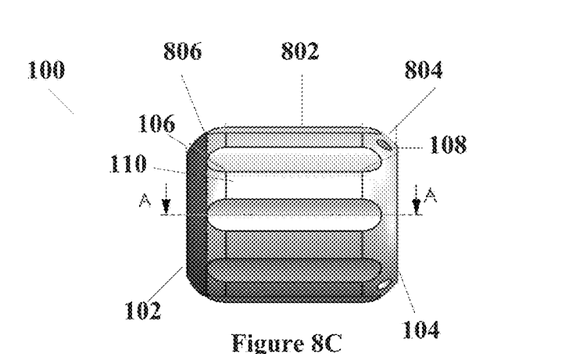
Figure 8D:
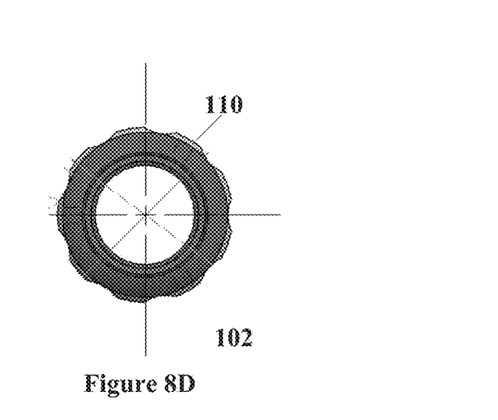
Figure 8E:
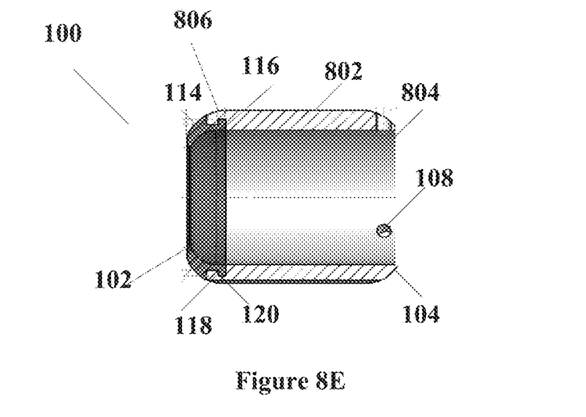

FIG. 6 illustrates a cross-section view of body 104 of skid 100 through the plane indicated by C-C in FIG. 4. This plane passes cross-sectionally through screw holes 108. As is illustrated in FIG. 6, screw holes 108 are positioned around body 104 and are separated by angles A2 and A3. Although there may be any number of screw holes 108 for holding set screws (not shown), FIG. 6 illustrates an embodiment with three screw holes 108. As is further illustrated in FIG. 6, screw holes 108 are tapped to accommodate a set screw of type S1.

Skid 100 can be sized to accommodate any inspection camera. In particular, the dimensions for an example skid 100 that can accommodate a 25 mm camera, a 34 mm camera, and a 45 mm are provided in Table I. Other sized cameras can be accommodated by adjusting the dimensions to fit the particular camera being used. Further, cameras having different shapes can be used with particular camera sizes. Consequently, the dimensions provided in Table I are examples only and are not intended to be limiting.

TABLE I

| Dimension ID | Dimension for a 25 mm Camera | Dimensions for a 34 mm Camera | Dimensions for a 46 mm camera |
|---|---|---|---|
| D1 | 33 mm | 42.50 mm | 61 mm |
| D2 | 26 mm | 34.50 mm | 46.20 mm |
| D3 | 23.63 mm | 25.60 mm | 36 mm |
| D4 | 25 mm | 34.50 mm | 36 mm |
| D5 | 19 mm | 25.60 mm | 36 mm |
| D6 | 27.50 mm | 37.50 mm | 49.2 mm |
| D7 | 29.50 mm | 40.50 mm | 52.2 mm |
| D8 | 30.20 mm | 42.5 mm | 55 mm |
| D9 | 8.0 mm | 8.2 mm | — |
| L1 | 26 mm | 54 mm | 40 mm |
| L2 | 7.50 mm | 3.30 mm | — |
| L3 | 2.50 mm | 3.0 mm | — |
| L4 | 4.50 mm | 5.0 mm | 13 mm |
| L5 | 9.0 mm | 10 mm | 15 mm |
| A1 | 40° | 40° | — |
| A2 | 120° | 120° | 120 |
| A3 | 120° | 120° | 120 |
| S1 | M4 | M4 | M4 |

FIGS. 7A through 7E illustrates various perspectives of a skid 100 as illustrated above. The Embodiment of skid 100 illustrates in FIGS. 7A through 7E include guide protrusions 704 formed in body 104 and complementary receptors 706 formed in front portion 102. Such protrusions 704 and receptors 706 allow front portion 102 to be positioned onto body 104 in a limited number of angular orientations, depending on the number of protrusion 704 and receptor 706 pairs. In some embodiments, protrusions 704 may be formed in front portion 102 while receptors 706 may be formed in body 104.

FIGS. 8A through 8E illustrate various perspectives of another example of skid 100 as discussed above. The example of skid 100 shown in FIGS. 8A through 8E includes an elongated body portion 802 along with a rear curved portion 804 and front curved portion 806. Elongated body portion 802 is a flat portion of body 104 that extends between curved portions 804 and 806. Front portion 102 attaches to front curved portion 806 while hole sets 108 are formed in curved portion 804.

Figure 9A:
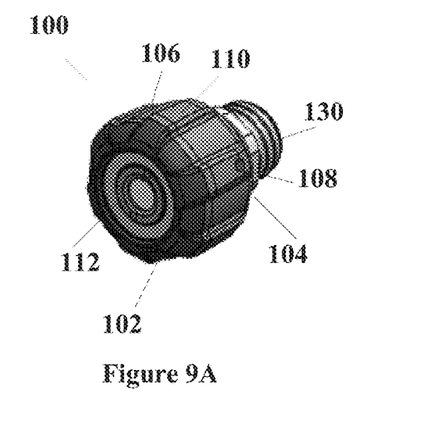
FIGS. 9A through 9E illustrate various perspectives of a camera skid according to some embodiments of the present invention.
Figure 9B:
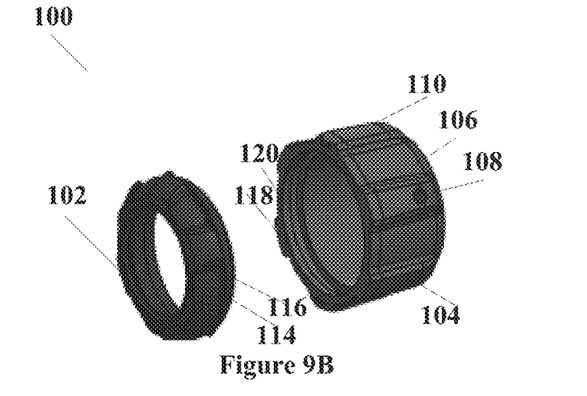
Figure 9C:
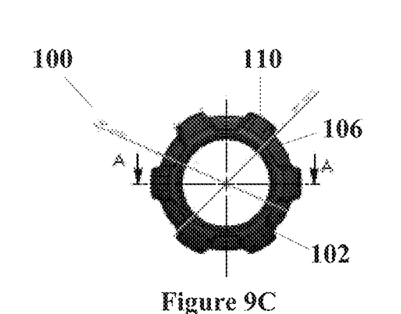
Figure 9D:
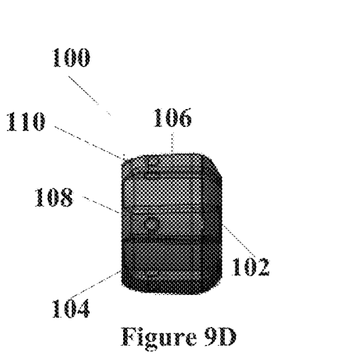
Figure 9E:
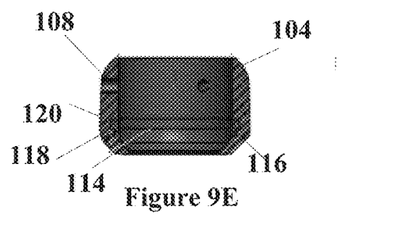

FIGS. 9A through 9E illustrates various perspectives of another example of skid 100 as discussed above. The example of skid 100 shown in FIGS. 9A through 9E have grooves 106 that are flat bottomed instead of circularly shaped, as is illustrated in FIG. 5. Furthermore, as is illustrated in FIG. 9D, body 104 is tapered instead of rounded or flat such that front portion 102 is inserted into the side with the greatest diameter.

In some embodiments, body 104 can be constructed of a rigid material such as, for example, hard plastic, aluminum, steel, rubber, or other rigid or semi-rigid material. Front portion 102 can be constructed of a pliable material such as rubber. As is further illustrated above, skid 100 can be formed in a number of different shapes and configurations that house a camera and allow camera inspections of various pipes.

In the preceding specification, various embodiments have been described with reference to the accompanying drawings. It will, however, be evident that various modifications and changes may be made thereto, and additional embodiments may be implemented, without departing from the broader scope of the invention as set for in the claims that follow. The specification and drawings are accordingly to be regarded in an illustrative rather than restrictive sense.

What is claimed is:

1. A camera skid, comprising:
    a body into which a camera can be inserted, wherein the body is constructed of a first material; and
    a front portion received into the body, the front portion including a lip that contacts a face of the camera, wherein the front portion is constructed of a pliable material less rigid than the first material;
    wherein the face of the camera is not completely covered by the front portion when the camera is in the skid.

2. The skid of claim 1, wherein the front portion includes a groove and a lip that mates with a body lip and a body groove formed in the body.

3. The skid of claim 1, wherein the body includes set screw holes that accommodate set screws to fix the camera in place.

4. The skid of claim 3, wherein the set screw holes are positioned at equal angular distances around the body.

5. The skid of claim 1, wherein the body includes ridges and includes grooves between the ridges, each groove and each ridge running in a direction from a first end of the body to a second end of the body, the first end being adjacent to the front portion, the second end being opposite from the front end, the grooves running through a widest portion of the camera skid for helping guide fluid in a pipe around the camera skid.

6. The skid of claim 5, wherein the grooves are circularly shaped.

7. The skid of claim 5, wherein the grooves are flat bottomed.

8. The skid of claim 1, wherein an outer diameter at a rear of the body is less than an outer diameter at a center of the body.

9. The skid of claim 1, wherein an outer diameter in a center of the body is a constant between two rounded edges.

10. The skid of claim 1, wherein the body is tapered.

11. The skid of claim 1, wherein the body includes protrusions and the front portion includes receivers for receiving the protrusions.

12. The skid of claim 1, wherein the front portion includes protrusions and the body includes receivers for receiving the protrusions.

13. A camera skid, comprising:
a body into which a camera can be inserted; and
a front portion received into the body, the front portion including a lip that contacts a face of the camera;
wherein the body includes ridges and includes grooves between the ridges, each groove and each ridge running in a direction from a first end of the body to a second end of the body, the first end being adjacent to the front portion, the second end being opposite from the front end, the grooves running through a widest portion of the camera skid for helping guide fluid in a pipe around the camera skid.

14. The skid of claim 13, wherein the body includes set screw holes that accommodate set screws to fix the camera in place.

15. A method for inspecting a pipe, the method comprising:
obtaining an assembly comprising an inspection camera and a camera skid, the camera having been inserted into a body of the skid;
imaging an interior of the pipe with the assembly, the imaging comprising:
inserting the assembly into the pipe; and
propelling the assembly down the pipe;
wherein the body includes ridges and includes grooves between the ridges, each groove and each ridge running in a direction from a face of the camera to a back of the camera through a widest portion of the camera skid;
wherein when the assembly has been inserted into the pipe, the camera skid keeps the camera off a floor of the pipe while at least one groove directs fluid in the pipe around the camera skid;
wherein the skid comprises a front portion received into the body, the front portion including a lip that contacts a face of the camera but does not cover the face of the camera, the front portion being constructed of a pliable material less rigid than the body;
wherein the face of the camera is not completely covered by the front portion when the camera is in the skid.

* * * * *